United States Patent [19]

Vatsala

[11] Patent Number: 4,921,800

[45] Date of Patent: May 1, 1990

[54] MICROBIAL PROCESS FOR PHOTOHYDROGEN PRODUCTION FROM CELLULOSE IN HIGH SALINE WATER MEDIUM

[76] Inventor: T. M. Vatsala, Shri A.M.M. Murugappa Chettiar Research Centre, Tharamani, Madras 600 013, India

[21] Appl. No.: 145,617

[22] Filed: Jan. 19, 1988

[51] Int. Cl.$^5$ .......................... C12P 3/00; C12R 1/01
[52] U.S. Cl. .................................. 435/168; 435/166; 435/170; 435/173; 435/822
[58] Field of Search ............... 435/168, 822, 170, 166, 435/173

[56] References Cited

U.S. PATENT DOCUMENTS 4,467,035  8/1984  Harasawa et al. ................... 435/268
4,532,210  7/1985  Miura et al. ........................... 435/822

OTHER PUBLICATIONS

Microbiology Arch (1984) 138: 251–256.

Primary Examiner—Herbert J. Lilling
Attorney, Agent, or Firm—Ladas & Parry

[57] ABSTRACT

A process that is carried out in partly sequential and partly simultaneous steps as detailed below, to build a process, with natural light using wave lengths from 360 nm to 900 nm using solid substrate of carbonaceous substances and one phototrophic bacteria and saline water to produce a rich fuel gas.

16 Claims, No Drawings

MICROBIAL PROCESS FOR PHOTOHYDROGEN PRODUCTION FROM CELLULOSE IN HIGH SALINE WATER MEDIUM

The following specification particularly describes and ascertains the nature of this invention and the manner in which it is to be performed.

Photogeneration of hydrogen by microbes is acquiring importance as a feasible route for energy generation. Among various attempts to photoproduce hydrogen using microbes, considerable attention has been paid to use of marine photosynthetic organisms. In what follows, we describe a novel method for photo-producing hydrogen using the marine photrophic bacterium, *Rhodospirillum salinarum.*

Recently, worldwide attention has been focused on the bioconversion of cellulosic residues into fuels food and energy. The major materials available for this purpose are from agricultural sources which are renewable. Therefore, development of a process for hydrogen production using solar energy, cellulosic materials and sea water is highly desirable.

Interest been focused on developing a process by which a marine thermophilic phototrophic bacterium *Rhodospirillum salinarum* ATCC 35394 (American Type Culture Collection, Rockville, Md.) which was isolated from Portugal by H. Nissen and D. Dundas is used for photohydrogen production with natural light and with organic acid and cellulose as substrates. Another advantage of using this strain is that it is thermophilic and can grow and produce H2 even at a temperature of 42 C. This strain was repeatedly subcultured on a medium described below with either DL-malic acid or cellulose as a carbon source until two pure strains were obtained: one which could grow on malate and also on cellulose.

The medium used was as described by Nissen and Dundas (Arch. Microbial., 130, 251–256, 1984) with one of the following carbon sources (1 g per liter of the medium):

(1) DL-malic acid
(2) microcrystalline cellulose.

Sea water connectrated to contain 10% sodium chloride was used for preparing the medium.

The media were sterilized by autoclaving and were sparged with ultra pure, sterile argon gas to remove traces of oxygen from the head space and medium and were inoculated with *R. salinarum* from the selected population maintained at 42 C. under diffused solar energy. The process runs were conducted with 1 l and 5 l glass and plastic vessels in a temperature range of 37–77 C. and illuminance of 15000 lux, provided by natural solar radiation. Samples of culture were periodically withdrawn from the process runs and were checked for growth on "Spectronic-20" spectrophotometer at a wavelength of 660 nm, using a predetermined calibration curve relating absorbance to dry weight of cells. The evolved gas was analyzed for gas composition on a gas chromatograph.

EXAMPLE

I give below data on photoproduction of hydrogen by *R. salinarum* utilizing DL-malic acid and cellulose as substrates.

| DAY | Growth (dry wt. mg/l culture) | | hydrogen produced (mg/g dry wt/day) | |
|---|---|---|---|---|
| | DL-malic acid | Cellulose | DL-malic | Cellulose |
| C | 10 | . | — | — |
| 14 | 500 | 530 | 42 | 40 |
| 22 | 1000 | 1050 | 26 | 20 |

The data presented above is meant to provide an example of the outcome of the process, which is of batch mode, and in no way implies its limits.

Summarizing the results I state:

(i) the organism is able to use solar energy, organic materials and concentrated sea water to produce $H_2$.

(ii) that the organism is able to produce $H_2$ even at temperatures as high as 42 C.

I claim:

1. A process for photogeneration of hydrogen, the process comprising:
   repeatedly selecting a particular population of *Rhodospirillum salinarum* in a saline water medium;
   combining said mineral medium with a solid substrate of carbonanceous substances;
   culturing said *Rhodospirillum salinarum* in the saline water medium and substrate;
   illuminating said *Rhodospirillum salinarum*, saline water medium and substrate with light in a wavelength range between 360 nm and 900 nm, the bacteria producing a rich fuel gas comprising hydrogen and carbon dioxide.

2. The process as claimed in claim 1 wherein said combining step is carried out with saline water medium prepared with concentrated sea water.

3. The process as claimed in claim 1 wherein said combining step is carried out with cellulose as the substrate.

4. The process as claimed in claim 1 wherein said combining step is carried out with malic acid as the substrate.

5. The process as claimed in claim 1 wherein said combining step is carried out with microcrystalline cellulose as the substrate.

6. The process as claimed in claim 1 further comprising the simultaneous step of exposing the *Rhodospirillum salinarum*, saline water medium and substrate to a temperature range between 38 to 42 degree centigrade.

7. A process for photogeneration of hydrogen, the process comprising:
   selecting a saline water medium;
   combining the saline water medium with a carbon source substance to form a substrate;
   inoculating the substrate with a selected population of *Rhodospirillum salinarum;*
   illuminating the *Rhodospirillum salinarum* and substrate with light of wavelengths between 360 nm to 900 nm.

8. The process as claimed in claim 7 wherein said combining step is carried out with DL malic acid as the carbon source substance.

9. The process as claimed in claim 7 wherein said combining step is carried out with cellulose as the carbon source substance.

10. The process as claimed in claim 7 wherein said combining step is carried out with microcrystalline cellulose as the carbon source substance.

11. The process as claimed in claim 7 further comprising a preparing step wherein said medium is prepared with concentrated sea water of 10% sodium chloride.

12. The process as claimed in claim 7 further comprising a sterilizing step wherein said medium is sterilized.

13. The process as claimed in claim 12 wherein the sterilizing step is carried out by autoclaving.

14. The process as claimed in claim 7 further comprising a sparging step.

15. The process as claimed in claim 14 wherein the sparging step is carried out by spraying the medium with ultra pure argon gas.

16. The process as claimed in claim 7 further comprising an exposing step wherein the medium and *Rhodospirillum salinarum* are exposed to a temperature range of 38–42 degrees centigrade.

* * * * *